United States Patent
Zamierowski (10) Patent No.: US 10,492,956 B2
(45) Date of Patent: *Dec. 3, 2019

(54) TOPICAL VACUUM-PRESS SURGICAL INCISIONAL DRESSINGS, SURGICAL ADJUNCTS, HYBRIDS AND COMPOSITES

(71) Applicant: KCI Licensing, Inc., San Antonio, TX (US)

(72) Inventor: David S. Zamierowski, Overland Park, KS (US)

(73) Assignee: KCI Licensing, Inc., San Antonio, TX (US)

( * ) Notice: Subject to any disclaimer, the term of this patent is extended or adjusted under 35 U.S.C. 154(b) by 277 days.

This patent is subject to a terminal disclaimer.

(21) Appl. No.: 15/285,418

(22) Filed: Oct. 4, 2016

(65) Prior Publication Data

US 2017/0020737 A1 Jan. 26, 2017

Related U.S. Application Data (63) Continuation-in-part of application No. 14/217,219, filed on Mar. 17, 2014, now Pat. No. 9,456,930.

(Continued)

(51) Int. Cl.
*A61F 13/00* (2006.01)
*A61F 13/02* (2006.01)
*A61M 1/00* (2006.01)

(52) U.S. Cl.
CPC .... *A61F 13/0216* (2013.01); *A61F 13/00068* (2013.01); *A61M 1/0088* (2013.01)

(58) Field of Classification Search
CPC .......... A61F 13/0216; A61F 13/00068; A61M 1/0088
See application file for complete search history.

(56) References Cited

U.S. PATENT DOCUMENTS 1,355,846 A  10/1920 Rannells
2,547,758 A   4/1951 Keeling
(Continued)

FOREIGN PATENT DOCUMENTS

AU   650575   8/1982
AU   745271  12/2002
(Continued)

OTHER PUBLICATIONS

Lavery, et al., "Emerging Concepts with VAC Therapy", Podiatry Today, vol. 20, Jul. 1, 2007, 1-6.

(Continued)

*Primary Examiner* — Kai H Weng
(74) *Attorney, Agent, or Firm* — Law Office of Mark Brown, LLC; Mark E. Brown (57) ABSTRACT

A negative pressure wound therapy (NPWT) dressing includes a wick configured for placement over an incision. A transfer assembly includes a compressible, porous core with a permeable cover placed over the core. The transfer assembly is positioned on the wick in fluidic contact and is covered by a dressing cover, which is configured for adhesive attachment to the patient around the incision. A drain slip including a proximal end configured for placement in the incision extends through the wick and the transfer assembly and is configured for connection to a negative pressure source. A NPWT method includes steps of draining a closed incision using negative pressure applied to a drain slip.

17 Claims, 1 Drawing Sheet

Related U.S. Application Data (60) Provisional application No. 61/800,224, filed on Mar. 15, 2013.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. |
| 3,115,138 A | 12/1963 | McEvenny et al. |
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,981,051 A | 9/1976 | Brumlik |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,248,232 A | 2/1981 | Engelbrecht et al. |
| 4,250,882 A | 2/1981 | Adair |
| 4,256,109 A | 3/1981 | Nichols |
| 4,259,959 A | 4/1981 | Walker |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errade et al. |
| 4,382,441 A | 5/1983 | Svedman |
| 4,392,853 A | 7/1983 | Muto |
| 4,392,858 A | 7/1983 | George et al. |
| 4,419,093 A | 12/1983 | Deaton |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,339 A | 8/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,696,301 A | 9/1987 | Barabe |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,775,909 A | 10/1988 | Inoue |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,976,726 A | 12/1990 | Haverstock |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,045,075 A | 9/1991 | Ersek |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,139,023 A | 8/1992 | Stanley et al. |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | Debusk et al. |
| 5,358,494 A | 10/1994 | Svedman |
| 5,383,897 A | 1/1995 | Wholey |
| 5,423,885 A | 6/1995 | Williams |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes et al. |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |
| 5,738,686 A | 4/1998 | Kubein-Meesenburg |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |
| 6,146,423 A | 11/2000 | Cohen et al. |
| 6,159,246 A | 12/2000 | Mendes et al. |
| 6,162,907 A | 12/2000 | Habener |
| 6,174,306 B1 | 1/2001 | Fleischmann |
| 6,179,804 B1 | 1/2001 | Satterfield |
| 6,190,391 B1 | 2/2001 | Stubbs |
| 6,190,392 B1 | 2/2001 | Vandewalle et al. |
| 6,203,563 B1 | 3/2001 | Fernandez |
| 6,241,747 B1 | 6/2001 | Ruff |
| 6,270,517 B1 | 8/2001 | Brotz |
| RE37,358 E | 9/2001 | Del Rio et al. |
| 6,287,316 B1 | 9/2001 | Agarwal et al. |
| 6,293,929 B1 | 9/2001 | Smith et al. |
| 6,345,623 B1 | 2/2002 | Heaton et al. |
| 6,355,215 B1 | 3/2002 | Poggie et al. |
| 6,377,653 B1 | 4/2002 | Lee et al. |
| 6,398,767 B1 | 6/2002 | Fleischmann |

(56) References Cited

U.S. PATENT DOCUMENTS

| | | |
|---|---|---|
| 6,430,427 B1 | 8/2002 | Lee et al. |
| 6,488,643 B1 | 12/2002 | Tumey |
| 6,493,568 B1 | 12/2002 | Bell et al. |
| 6,500,209 B1 | 12/2002 | Kolb |
| 6,503,281 B1 | 1/2003 | Mallory |
| 6,540,705 B2 | 4/2003 | Norstrem et al. |
| 6,553,998 B2 | 4/2003 | Heaton et al. |
| 6,589,285 B2 | 7/2003 | Penenberg |
| 6,620,132 B1 | 9/2003 | Skow |
| 6,626,891 B2 | 9/2003 | Ohmstede |
| 6,645,226 B1 | 11/2003 | Jacobs et al. |
| 6,669,735 B1 | 12/2003 | Pelissier |
| 6,685,681 B2 | 2/2004 | Lockwood et al. |
| 6,695,823 B1 | 2/2004 | Lina et al. |
| 6,695,824 B2 | 2/2004 | Howard et al. |
| 6,726,706 B2 | 4/2004 | Dominguez |
| 6,752,794 B2 | 6/2004 | Lockwood et al. |
| 6,764,462 B2 | 7/2004 | Risk et al. |
| 6,800,074 B2 | 10/2004 | Henley et al. |
| 6,814,079 B2 | 11/2004 | Heaton et al. |
| 6,824,533 B2 | 11/2004 | Risk et al. |
| 6,828,468 B2 | 12/2004 | Ansmann et al. |
| 6,856,821 B2 | 2/2005 | Johnson |
| 6,860,903 B2 | 3/2005 | Mears et al. |
| 6,936,037 B2 | 8/2005 | Bubb |
| 6,951,553 B2 | 10/2005 | Bubb et al. |
| 6,953,480 B2 | 10/2005 | Mears et al. |
| 6,991,643 B2 | 1/2006 | Saadat |
| 7,070,584 B2 | 7/2006 | Johnson et al. |
| 7,105,021 B2 | 9/2006 | Edens et al. |
| 7,108,683 B2 | 9/2006 | Zamierowski |
| 7,381,211 B2 | 6/2008 | Zamierowski |
| 7,645,269 B2 | 1/2010 | Zamierowski |
| 7,976,519 B2 | 7/2011 | Bubb et al. |
| 3,366,693 A1 | 2/2013 | Hu et al. |
| 3,394,081 A1 | 3/2013 | Locke et al. |
| 9,456,930 B2 | 10/2016 | Zamierowski |
| 2002/0022861 A1 | 2/2002 | Jacobs et al. |
| 2002/0029063 A1 | 3/2002 | Wittmann |
| 2002/0143286 A1 | 10/2002 | Tumey |
| 2004/0006319 A1 | 1/2004 | Lina et al. |
| 2005/0043818 A1 | 2/2005 | Bellon et al. |
| 2006/0079852 A1 | 4/2006 | Bubb et al. |
| 2007/0038172 A1 | 2/2007 | Zamierowski |
| 2008/0208171 A1 | 8/2008 | Argenta et al. |
| 2009/0012483 A1* | 1/2009 | Blott ............... A61M 1/0088 604/315 |
| 2009/0227969 A1 | 9/2009 | Jaeb et al. |
| 2011/0092927 A1 | 4/2011 | Wilkes et al. |

FOREIGN PATENT DOCUMENTS

| | | |
|---|---|---|
| AU | 755496 | 12/2002 |
| CA | 2005436 | 6/1990 |
| DE | 2640413 | 3/1978 |
| DE | 4306478 | 9/1994 |
| DE | 29504378 | 9/1995 |
| EP | 0100148 | 2/1984 |
| EP | 0117632 | 9/1984 |
| EP | 0161865 | 11/1985 |
| EP | 0358302 | 3/1990 |
| EP | 1018967 | 8/2004 |
| EP | 1513478 | 12/2009 |
| GB | 692578 | 6/1953 |
| GB | 2195255 | 4/1988 |
| GB | 2197789 | 6/1988 |
| GB | 2220357 | 1/1990 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | WO9011795 | 10/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 04/60148 | 7/2004 |
| WO | 2011008360 | 1/2011 |

OTHER PUBLICATIONS

Letsou, M.D. et al. "Stimulation of Adenylate Cyclase Activity in Cultured Endothelial Cells Subjected to Cyclic Stretch", Journal of Cardiovascular Surgery, 31, 1990, 534-539.

Manwaring, et al., "Characterization of Rat Meningeal Cultures on Materials of Differing Surface Chemistry", Biomaterials, vol. 22, 2001.

Manwaring, et al., "Contact Guidance Induced Organization of Extracellular Matrix", Biomaterials, vol. 25, 2003, 3631-3638.

Masters, "Letter to the Editor", British Journal of Plastic Surgery, vol. 51(3), 1998; Elsevier Science/The British Association of Plastic Surgeons, UK, 267.

Mendez-Eastman, RN, "When Wounds Won't Heal", RN, Jan. 1998, vol. 61(1), Medical Economics Company, Inc., Montvale, NJ, USA, 20-24.

Mercier, et al., "Poly(lactide-co-glycolide) microspheres as a moldable scaffold for Cartilage Tissue Engineering", Biomaterials, vol. 26, 2005, 1945-1952.

Meyer, et al., "A New Abdominal Drain for Overflowing Lavage in Instances of Severe Pancreatitis with Persistent Peritoneal Contamination", Surgery, Gynecology & Obstetrics, vol. 165, Sep. 1987.

Meyer, et al., "Selections from Bier's Hyperemic Treatment in Surgery, Medicine, and the Specialties: A Manual of Its Practical Application", W.B. Sunders Co., 2 Ed., 1909, 17-25, 44-64, 90-96, 167-170, and 210-211.

Mikos, et al., "Preparation of Poly(glycolic acid) Bonded Fiber Structures for Cell Attachment and Transplantation", Journal of Biomedical Materials Research, vol. 27, 1993, 183-189.

Miyauchi, et al., "Repair of Incisional Hernia with Prolene Hernia System", The Journal of Medical Investigation, vol. 50, p. 108-111, 2003; received for publication Aug. 8, 2002.

Morykwas, et al., "Vacuum-Assisted Closure: A new Method for Wound Control and Treatment: Animal Studies and Basic Foundation", Annals of Plastic Surgery, vol. 38, No. 6, 1997, 553-562.

Norman, et al., "Methods for Fabrication of Nanoscale Topography for Tissue Engineering Scaffolds", Annals of Biomedical Engineering, vol. 34, No. 1, Jan. 2006, 89-101.

Orringer, et al., "Management of Wounds in Patients with Complex Enterocutaneous Fistulas", Surgery, Gynecology & Obstetrics, vol. 165, Jul. 1987, 79-80.

Pailler-Mattei, et al., "Study of Adhesion Forces and Mechanical Properties of Human Skin in vivo", J. Adhesion Sci. Technol., vol. 18, No. 15-16, 2004, 1739-1758.

Pfister, et al., "Neural Engineering to Produce In Vitro Nerve Constructs and Neurointerface", Neurosurgery: www.neurosurgery-online.com, 2007, 137-142.

Poritz, et al., "Percutaneous Drainge and Ileocolectomy for Spontaneus Intraabdominal Abscess in Chrohn's Disease", J. Gast. Surg., vol. 11, Jan. 19, 2007, 204-207.

Puyana, "Resuscitation of Hypovolemic Shock", Textbook of Critical Care, 5th Ed., Ch. 229, 2005, 1933-1943.

Reckard, et al., "Management of Intraabdominal Hypertension by Percutaneous Catheter Drainage", JVIR, vol. 16, No. 7, Jul. 2005, 1019-1021.

Robledo-Ogazon, et al., "Using the Vacuum Assisted Closure System VAC in the Treatment of Infected Surgical Wounds. Clinical Experience", madigraphic Artemisa, vol. 74, No. 2, Mar.-Apr. 2006, 107-113.

Sachlos, et al., "Making Tissue Engineering Scaffolds Work. Review on the Application of Solid Freeform Fabrication Technology to the Production of Tissue Engineering Scaffolds", European Cells and Materials, vol. 5, 2003, 29-40.

(56) References Cited

OTHER PUBLICATIONS

Safronov, "Vacuum Therapy of Trophic Ulcers of the Lower Leg with Simultaneous Autoplasty of the Skin", Ministry of Public Health of the USSR, 1967, 1-50.

Saxena, et al., "Vacuum-Assisted Closure: Microdeformations of Wounds and Cell Proliferation", Plast Reconstr Surg., 114(5), Oct. 2004, 1086-1096.

Schein, et al., "The 'sandwich technique' Management of the Open Abdomen", Br. J. Surg., vol. 73, May 1986, 369-370.

Segvich, et al., "Uniform Deposition of Protein Incorporated Mineral Layer on Three-Dimensional Porous Polymer Scaffolds", Journal of Biomedical Materials Research Part B: Applied Biomaterials 84B(2): <http://hdl.handle.net/2027.42/57926>, May 8, 2007, 340-349.

Sherck, et al., "Covering the "Open Abdomen": A Better Technique", The American Surgeon, vol. 64, Sep. 1998.

Shimko, et al., "Effect of Porosity on the Fluid Flow Characteristics and Mechanical Properties of Tantalum Scaffolds", Journal of Biomedical Materials Research, Part B, Applied Biomaterials, Sep. 24, 2004, 315-324.

Solovev, et al., "The Method of Treatment of Immature External Fistulas in the Upper Gastrointestinal Tract", S.M. Kirov Gorky State Medical Institute, 1987, 1-20.

Solovev, "Treatment and Prevention of Suture Failures After Gastric Resection", S.M. Kirov Gorky State Medical Institute, 1988, 1-55.

Stannard, et al., "Use of negative pressure wound therapy over clean, closed surgical incisions", International Wound Journal, 2012 vol. 9 (Suppl. 1), Aug. 2012, 32-39.

Svedman, "A Dressing Allowing Continuous Treatment of a Biosurface", IRCS Medical Science: Biomedical Technology; Clinical Medicine; Surgery and Transplantation, Jul. 1979, 221.

Svedman, et al., "A Dressing System Providing Fluid Supply and Suction Drainage Used for Continuous or Intermittent Irrigation", Annals of Plastic Surgery, vol. 17, No. 2, Aug. 1986, 125-133.

Svedman, "Irrigation Treatment of Leg Ulcers", The Lancet, vol. 322, Issue 8349, Sep. 3, 1983, 532-534.

Takahashi, et al., "Induction of Pluripotent Stem Cells from Mouse Embryonic and Adult Fibroblast Cultures by Defined Factors", Cell, vol. 126, Aug. 25, 2006, 663-676.

Tan, et al., "Inhibition of Osteocyte Apoptosis by Fluid Flow is Mediated by Nitric Oxide", Biochemical and Biophysical Research Communications, vol. 369, Issue 4, May 16, 2008, 1150-1154.

Tan, et al., "Osteocytes Subjected to Fluid Flow Inhibit Osteoclast Formation and Bone Resorption", Bone, vol. 4, Jul. 27, 2007, 745-751.

Tennant, "The Use of Hyperemia in the Postoperative Treatment of Lesions of the Extremities and Thorax", Jour. A.M.A., May 8, 1915, 1548-1549.

Timmenga, et al., "The Effect of Mechanical Stress on Healing Skin Wounds: An Experimental Study of Rabbits Using Tissue Expansion", British Journal of Plastic Surgery, vol. 44, 1991, 514-519.

Tribble, "An Improved Sump Drain-Irrigation Device of Simple Construction", Arch. Surg., vol. 105, Sep. 1972, 511-513.

Venturi, et al., "Mechanisms and CLinical Applications of the Vacuum-Assisted Closure (VAC) Device", Am. J. Clin. Dermatol., vol. 6 (3), 2005, 185-194.

Walsh, et al., "Directional Neurite Outgrowth Is Enhanced by Engineered Meningeal Cell-Coated Substrates", Tissue Engineering, vol. 11, No. 7/8, Mary Ann Liebert, Inc., 2005, 1085-1095.

Wilkes, et al., "3D Strain Measurement in Soft Tissue: Demonstration of a Novel Inverse Finite Element Model Algorithm on MicroCT Images of a Tissue Phantom Exposed to Negative Pressure Wound Therapy", Journal of the Mechanical Behavior of Biomedical Materials, Nov. 5, 2008, 1-16.

Yusupov, et al., "Active Wound Drainage", Vestnik Khirurgi, vol. 138, Issue 4, 1987, 42-46.

Zivadinovic, et al., "Vacuum Therapy in the Treatment of Peripheral Blood Vessels", Conference Papers of the 5th Timok Medical Days, Timok Medical Journal, Majdanpek, Copy and Certified Translation, 1986, 161-164.

"V.A.C. Therapy Clinical Guidelines: A Reference Source for Clinicians", KCI: The Clinical Advantage, Jul. 2007, 1-92, 28.

Aktiengesellschaft, "Opposition to EP1513478", Sep. 16, 2010.

Ambrosio, et al., "V.A.C. GranuFoam Silver Dressing a New Antimicrobial Silver Foam Dressing Specifically Engineered for Use with V.A.C. Therapy", http://silverlon.com/fda.html, retrieved from the Internet Jul. 27, 2006, 1-71.

Anderson, et al., "Design of Tissue Engineering Scaffolds as Delivery Devices for Mechanical and Mechanically Modulated Signals", Tissue Engineering, vol. 13, No. 10, 2007, 2525-2539.

Arcand, et al., "Negative Pressure Wound Therapy and Its Application to Orthopaedics. Part II: Clinical Application", Osteo Trauma Care, 2006, 254-258.

Argenta, et al., "Vacuum-Assisted Closure: A New Method for Wound Control and Treatment: Clinical Experience", Annals of Plastic Surgery, vol. 38, No. 6, Jun. 1997, 563-576.

Armstrong, et al., "Planter Pressure Changes Using a Novel Negative Pressure Wound Therapy Technique", Journal of the Am. Podiatric Med. Assoc., vol. 94, No. 5, Sep. 2004, 456-460.

Arnljots, et al., "Irrigation Treatment in Split-Thickness Skin Grafting of Intractable Leg Ulcers", Scand J. Plast. Reconstr. Surg., 19, Nov. 19, 1984, 211-213.

Bagautdinov, "Variant of External Aspiration in the Treatment of Purulent Diseases of Soft Tissues", Ministry of Higher and Secondary Education of the RSFSR I.N. Ulyanov Chuvash State University, 1986, 94-96.

Baig, et al., "Percutaneous Postoperative Intra-Abdominal Abscess Drainage After Elective Colorectal Surgery", Tech Coloproctol, vol. 6, 2002, 159-164.

Barker, et al., "Vacuum Pack Technique of Temporary Abdominal Closure: A 7-Year Experience with 112 Patients", The Journal Trauma: Injury, Infection and Critical Care, vol. 48, No. 2, Feb. 2000, 201-207.

Blackburn, II, MD, "Negative-Pressure Dressings as a bolster for Skin Grafts", Annals of Plastic Surgery, vol. 40, No. 5, May 1998, 453-457.

Boersma, et al., "Photogrammetric Wound Measurement with a Three-Camera Vision System", IAPRS, vol. 33, 2000.

Brabmamdam, et al., "Critical Care I", Surg. Forum Abstracts, vol. 207, No. 3S, Sep. 2008, S34-S35.

Brock, et al., "Temporary Closure of Open Abdominal Wounds: The Vacuum Pack", The Am. Surgeon,, Jan. 1995, 30-35.

Brody, et al., "Approaches to Heart Valve Tissue Engineering Scaffold Design", Journal of Biomedical Materials Research Part B: Applied Biomaterials, 2006, 16-43.

Burdette, et al., "Systemic Inflammatory Response Syndrome", eMedicine Critical Care; http://emedicine.medscape.com/article/168943-print, Apr. 16, 2007, 1-19.

Chariker, et al., "Effective Management of Incisional and Cutaneous Fistulae with Closed Suction Wound Drainage", Contemporary Surgery, vol. 34, Jun. 1989, 59-63.

Cheboksary, "Current Problems in Modern Clinical Surgery Interdepartmental Collection", Ministry of Higher and Secondary Education of the RSFSR I.N. Ulyanov Chuvash State University, May 21, 1986, 1-153.

Chinn, et al., "Closed Wound Suction Drainage", The Journal of Foot Surgery, vol. 1, No. 1, 1985, 76-81.

Culliford, et al., "A Novel Technique for Vacuum Assisted Closure Device Application in Noncontiguous Wounds", Journal of Plastic, Reconstructive and Aesthetic Surgery, 2006, 1-2.

Cunningham, "Development of in-vitro Model to Simulate Dermal Wound Bed Interaction with Granufoam and Gauze Dressing Under Sub Atmospheric Pressure", Micro CT Study—Test Cell Development, Report, Jul. 30, 2006, 1-19.

Dattilo, Jr., et al., "Medical Textiles: Application of an Absorbable Barbed Bi-directional Surgical Suture", Journal of Textile and Apparel, Technology and Management, vol. 2, Issue 2, Spring 2002, 1-5.

Davydov, et al., "Bacteriological and Cytological Assessment of Vacuum Therapy of Purulent Wounds", Vestnik Khirurgi, Oct. 1998, 48-52.

(56) References Cited

OTHER PUBLICATIONS

Davydov, et al., "Concepts for the Clinical-Biological Management of the Wound Process in the Treatment of Purulent Wounds by Means of Vacuum Therapy", Vestnik Khirurgi, Jul. 7, 1980, 132-136.

Davydov, et al., "Vacuum Therapy in the Treatment of Purulent Lactation Mastitis", Vestnik Khirurgi, May 14, 1986, 66-70.

Dee, "The Successful Management of a dehisced Surgical Wound with TNP Following Femoropopliteal Bypass", Journal of Wound Care, vol. 16, No. 1, Jan. 2007, 42-44.

Delalleau, et al., "Characterization of the Mechanical Properties of Skin by Inverse Analysis Combined with the Indentation Test", Journal of Biomechanics, vol. 39, 2006, 1603-1610.

Diridollou, et al., "In vivo Model of the Mechanical Properties of the Human Skin Under Suction", Skin Research and Technology, vol. 6, 2000, 214-221.

Dubick, et al., "Issues of Concern Regarding the Use of Hypertonic/Hyperoncotic Fluid Resuscitation of Hemorrahagic Hypotension", Shock, vol. 25, No. 4, 2006, 321-328.

Egnell Minor, "Addition to the User's Manual Concerning Overflow Protection", Industrigaton2, 461, 37 Trollhattan, Feb. 3, 1983, 2.

Egnell Minor, "Egnell Minor Instruction Book, 1st Edition, 300 7502", Feb. 1975, 1-24.

Fong, et al., "Initial Clinical Experience Using a Novel Ultraportable Negative Pressure Wound Therapy Device", Wounds, a Compendium of Clinical Research and Practice, vol. 22 Issue 9., Sep. 2010, 230-236.

Garner, et al., "Vacuum-Assisted Wound Closure Provides Early Fascial Reapproximation in Trauma Patients with Open Abdomens", The Am. Journ. Surg, vol. 182, 2001, 630-638.

Gemmiti, et al., "Fluid Flow Increases Type II Collagen Deposition and Tensile Mechanical Properties in Bioreactor-Grown Tissue-Engineered Cartilage", Tissue Engineering, vol. 12, No. 3, 2006, 469-479.

Grauhan, et al., "Prevention of Poststernotomy Wound Infections in Obese Patients by Negative Pressure Wound Therapy", The Journal of Thoracic and Cardiovascular Surgery, vol. 145, No. 5., May 2013, pp. 1387-1392.

Greer, et al., "The Use of Subatmospheric Pressure Dressing Therapy to Close Lymphocutaneous Fistulas of the Groin", British Journal of Plastic Surgery (2000), 53, 484-487.

Gupta, et al., "Guidelines for Managing Pressure Ulcers with Negative Pressure Wound Therapy", Supplement to Advances in Skin and Wound Care, vol. 17, Supp. 2, Nov. 2004, 1-16.

Herte, et al., "Comparative Wound Healing in Animal Subjects Using the Cuba System VS Conventional Surgical Instruments", The American Society of Plastic and Reconstructive Surgeons, Nov. 1978, 1-19.

Jeschke, et al., "Development of New Reconstructive Techniques: Use of Integra in Combination with Fibrin Glue and Negative-Pressure Therapy fro Reconstruction of Acute and Chronic Wounds", Departments of General Surgery and Trauma and Reconstructive Surgery, University of Regensburg, Jan. 15, 2003, 525-530.

Jeter, et al., "Managing Draining Wounds and Fistulae: New and Established Methods", Chronic Wound Care: Health Management Publications, 1990, 240-246.

Johnson, "An Improved Technique for Skin Graft Placement Using a Suction Drain", Surgery, Gynecology & Obstetrics, vol. 159, Dec. 1984, 585-586.

Kaplan, et al., "Guidelines for the Management of the Open Abdomen", Supplement to Wounds, Oct. 2005, 1-26.

Khatyr, "Model of the Viscoelastic Behaviour of Skin in vivo and Study of Anisotropy", Skin Research and Technology, vol. 10, 2004, 96-103.

Kostyuchenok, et al., "Vacuum Treatment in the Surgical Management of Purulent Wounds", Vestnik Khirugi, Sep. 1986, 18-21.

Kuznetsov, et al., "Vacuum and Vacuum-Sorption Treatment of open Septic Wounds, Appendix B", II AII-Union Conference on Wounds and Wound Infections: Presentation Abstracts Moscow, U.S.S.R., Oct. 29, 1986, 91-92.

Kwan, et al., "A Structural Model to Describe the Nonlinear stress-Strain Behavior for Parallel-Fibered Collagenous Tissues", Journal of Biomechanical Engineering, vol. 111, Nov. 1989, 361-363.

Lago, et al., "Neurobiological Assessment of Regenerative Electrodes for Bidirectional Interfacing Injured Peripheral Nerves", IEEE Transactions on Biomedical Engineering, vol. 54, No. 6, Jun. 2007, 1129-1137.

Laskin, "Minimally Invasive Total Knee Replacement Using a Mini-Mid Vastus Incision Technique and Results", Surgical Technology International, vol. 13, 2004, 231-238.

Latenser, et al., "A Pilot Study Comparing Percutaneous Decompression with Decompressive Laparotomy for Acute Abdominal Compartment Syndrome in Thermal Injury", Journal of Burn Care & Rehab., vol. 23, No. 3, May/Jun. 2002, 190-195.

"Algorithm for Abdominal Wall Construction", Plastic and Reconstructive Surgery, Jan. 2000, 207-209.

"All Silicone Jackson Pratt Style Flat Drain", C. Daniel Medical, Inc., retrieved from internet Mar. 15, 2007, http://www.cdanielmedical.com/flat-drain.html, 1-2.

"All Silicone Jackson Pratt Style Round Drain", C. Daniel Medical, Inc., retrieved from internet Mar. 15, 2007, http://www.cdanielmedical.com/round-drain.html, 1-2.

"Antibacterial Silver Wound Dressing, Bandage, Gauze and Adhesive Strips", Silverlon Woundcare Products; http://www.silverlon.com/wound.htm; retrieved from Internet Jul. 27, 2006, 1-5.

"Extended European Search Report", European Patent Application No. 14763938.9, dated Mar. 24, 2016, pp. 1-7.

"Hydrophobic Rigid Canisters", http://www.bemishealthcare.com/docs/anisterHydrophobic; Retrieved from Internet Mar. 15, 2007, 1-1.

"International Preliminary Examination Report and Search Report", PCT/GB96/02802, dated Jan. 15, 1998 and Apr. 29, 1997.

"International Search Report", PCT/GB98/02713, dated Jan. 8, 1999.

"International Search Report", PCT/GB95/01983, dated Nov. 23, 1995.

"International Search Report and Written Opinion", PCT/US2013/069756, dated Jan. 30, 2014, 1-10.

"International Search Report and Written Opinion", PCT/US2014/030860, dated Sep. 8, 2014, pp. 1-12.

"NPD 1000 Negative Pressure Wound Therapy System", Kalypto Medical: www.kalyptomedical.com, Sep. 2008, 1-4.

"Occlude", Merriam Webster Online Dictionary; http://www.merriam-webster.com/dictionary/occlude; retrieved from Internet Mar. 4, 2008.

"Patentee's Observations on the Oppositions", KCI Licensing, Inc. Response to Opponents Smith & Nephew, Inc., and Paul Hartmann Aktiengesellschaft Oppositions, Apr. 21, 2011, 1-15.

"PCT Written Opinion", PCT/GB98/02713, dated Jun. 8, 1999.

"PCT Written Opinion", PCT/GB96/028202, dated Sep. 3, 1997.

"Search Report and Written Opinion of the International Search Authority", International Application No. PCT/US06/38855 filed Oct. 3, 2006, report dated Aug. 8, 2007.

"Smith & Nephew, Inc. Opposition against EP 1,513,478", Sep. 16, 2010.

Grauhan, et al., "Prevention of Poststemotomy Wound Infections in Obese Patients by Negative Pressure Wound Therapy", The Journal of Thoracic and Cardiovascular Surgery, vol. 145, No. 5., May 2013, pp. 1387-1392.

\* cited by examiner

TOPICAL VACUUM-PRESS SURGICAL INCISIONAL DRESSINGS, SURGICAL ADJUNCTS, HYBRIDS AND COMPOSITES

CROSS-REFERENCE TO RELATED APPLICATIONS

This application is a continuation-in-part of and claims priority in U.S. patent application Ser. No. 14/217,219, filed Mar. 17, 2014, now U.S. Pat. No. 9,456,930, issued Oct. 4, 2016, which claims priority in U.S. Provisional Patent Application Ser. No. 61/800,224, filed on Mar. 15, 2013. Both applications are owned by a common assignee herewith asked, and are incorporated herein by reference. The following patents and published patent applications are related and are also incorporated herein by reference: U.S. Pat. No. 6,951,553, issued on Oct. 4, 2005; U.S. Pat. No. 6,936,037, issued on Aug. 30, 2005; U.S. Pat. No. 7,976,519, issued on Jul. 12, 2011; U.S. Pat. No. 8,956,335, issued on Feb. 17, 2015; U.S. Pat. No. 9,408,956, issued on Aug. 9, 2016, and U.S. patent application Ser. No. 14/442,388, filed on May 12, 2015.

BACKGROUND OF THE INVENTION

1. Field of the Invention

The present invention relates generally to negative pressure wound therapy (NPWT) and in particular to dressings for surgical incisions.

2. Description of the Related Art

Current external or topical vacuum-assisted dressings (also referred to as negative pressure wound therapy (NPWT) systems (e.g., post-surgical, incisional dressing systems)) have been shown to quickly (e.g., possibly within a few hours) seal and close the dermal-epidermal portion of the skin incision (side-to-side). This has the consequence (clearly evident in several clinical studies now) of preventing surface bacteria from entering the incisional space or the wound below and thus preventing incisional or surgical wound infection, particularly superficial infection.

An area of investigation relates to the "deep" sub-dermal effects of topical vacuum-press systems and treatment procedures. For example, an investigational topic relates to the prevention or reduction of the effects of seroma and hematoma. Another area of investigation concerns how far sub-dermal or deep in the incision/surgical wound is there an effect of the dressing on the surface.

Previous systems have used rayon-wrapped Granufoam dressing material (Kinetic Concepts, Inc. of San Antonio, Tex.) and NPWT techniques on the skin surface with a liner, routinely accompanied by large dissection space procedures with deep "Hemovac-type" drains brought out through separate stab wounds peripheral to the incision. Differences in the behavior of these drains have been observed clinically compared to the drainage characteristics known to occur without the external vacuum-assisted dressing, indicating that post-incisional dressings effected outcomes. Without this vacuum-press type surface dressing, these Hemovac-type drains would have a significant measureable amount of drainage over the first few days, then decreasing to what is considered an "irritation" level of drainage (10-20 cc's of clear yellow serum—i.e., no bleeding, just the amount of reactive drainage associated with the simple presence of this plastic tube in the tissue preventing complete apposition of the tissue by its presence).

The concept is that this amount of drainage would continue day after day as long as the tube was in place. But with a NPWT type of dressing in place, drainage during the first few post-incision days can be significantly decreased—essentially to irritation levels. In fact, oozing into the drain, after closure of the incision, has sometimes been observed to suddenly stop after the foam dressing is compressed with the drains placed deeply, e.g., at fascia level. So it was felt that deep bleeding ceased when the vacuum-press dressing was compressed using NPWT procedures. These observations suggest that vacuum-press post-operative dressings decrease hematoma and seroma formation.

As an incision is being closed, tissue voids, pockets, spaces and irregularities may prevent firm tissue-to-tissue apposition and create an actual "space." This is quickly filled by fluid—depending on the circumstances, this fluid consists of a spectrum from pure blood to pure extracellular and lymph fluid without any blood or serum clotting factors. The initial behavior of this fluid collection depends on which side of the spectrum it is. If there is enough pure blood to clot, this will be a hematoma. The consequence of any "space-occupying" hematoma is that the process of clot lysis, which proceeds over several days, carries with it the risk of "unclotting" blood vessels of sufficient size and pressure such that rebleeding occurs and causes a post-operative complication of an "expanding hematoma."

If re-bleeding does not occur, problems can occur with probable expansion at both ends of this spectrum of fluid in a space. Lysis, cell and clot breakdown with the freeing of protein can all produce particles that create an osmotic pressure. If this is greater than the absorptive capability, the fluid expands rather than contracts. If that occurs early before there is any collagen production with strength, then this breaks apart the surrounding tissue apposition (aided by any irregular tension from the suture position, necrosis from just the presence and nature of the suture ligatures, cautery debris, surface of the incision trauma from the very act of surgery, etc.). In other words, one can think of the dissection space of an operation as easier to be again split apart than to be held together.

So, even in a relatively pure seroma that never had any significant amount of blood in it to start with, there is still enough oncotic pressure from the unabsorbed large proteins such that expansion becomes a greater force than absorption and that, plus the simple mechanics of the presence of liquid between layers preventing collagen bridging and development of any strength between opposing layers of tissue, allows us to see that seromas also "expand" and we can see how just their very presence is a potentiating factor for "dehiscence."

If we look at the above scenarios, we get another glimpse at what NPWT-incisional dressings or topical vacuum pack dressings systems seem to be doing: they are changing the healing process during the critical first 48 hours of wound healing. Because the dressing enhances and enables tissue apposition, not only at the surface but also at levels beneath the dressing, it reduces and prevents the early increase in size of liquid-filled space lesions in incisions. But a review of the current data suggests that it does not take away a space-occupying fluid collection that is already there on completion of the closure before a NPWT-incisional dressing is applied, e.g., in the operating room. Use of a buried suction drain such as a Hemovac drain may reduce this. But looking at these dynamics in this way suggests another alternative.

If we look at methods to decrease the presence of liquid-filled space-occupying lesions (i.e. hematoma/seroma) at the moment the incision is compressed on the operating table, we see an alternative to Hemovac drains brought out through a separate stab wound and left for several days, and to the option of preventing complete sealing of the incision by placing Swanson-type or wick drains through the incision, at its end or between sutures and leaving them for 24 to 72 hours to allow the incision to drain, and then having to change the entire topical vacuum-pack system, and that alternative is to drain the hematoma/seroma collections that form during closure on the operating table just before or, preferably, just after the foam core in the external dressing is compressed and then remove the drain and seal the dressing before the patient leaves the operating room.

Again, this entire concept can be summarized by the idea of the "set" of the wound or incision. Orthopedic surgeons reduce and hold fractures in position as the plaster cast is applied. Plastic surgeons roll and "milk" wounds to get everything drained and in a suspended new position before the wrap or tape or garment is applied to hold this "set." General surgeons use "retention" sutures and large ligatures to hold at-risk abdominal incision closures in place.

External vacuum-assisted NPWT systems use dressings that are eminently suited to hold the tissues in set apposition. The task then is to formalize the final removal of still-present drainage and to arrange the set of the wound as the foam core compresses. This disclosure then is to propose alternative methods and materials to accomplish that for both the peel-and-place and the customizable NPWT systems.

SUMMARY OF THE INVENTION

In the practice of the present invention, topical, NPWT surgical incisional systems and methods are provided, which can include surgical adjuncts, hybrids and composites. Wound therapy can be utilized with these systems and methods for facilitating wound healing and reducing potential complications, including prevention of liquid-filled space-occupying lesions, such as seroma and hematoma.

Other objects and advantages of the present invention will be apparent from the following description. Detailed descriptions of exemplary embodiments are provided in the following sections. However, the invention is not limited to such embodiments.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

As required, detailed aspects of the present invention are disclosed herein; however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, up, down, front, back, right and left refer to the invention as orientated in the view being referred to. The terms "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

Figure 1:
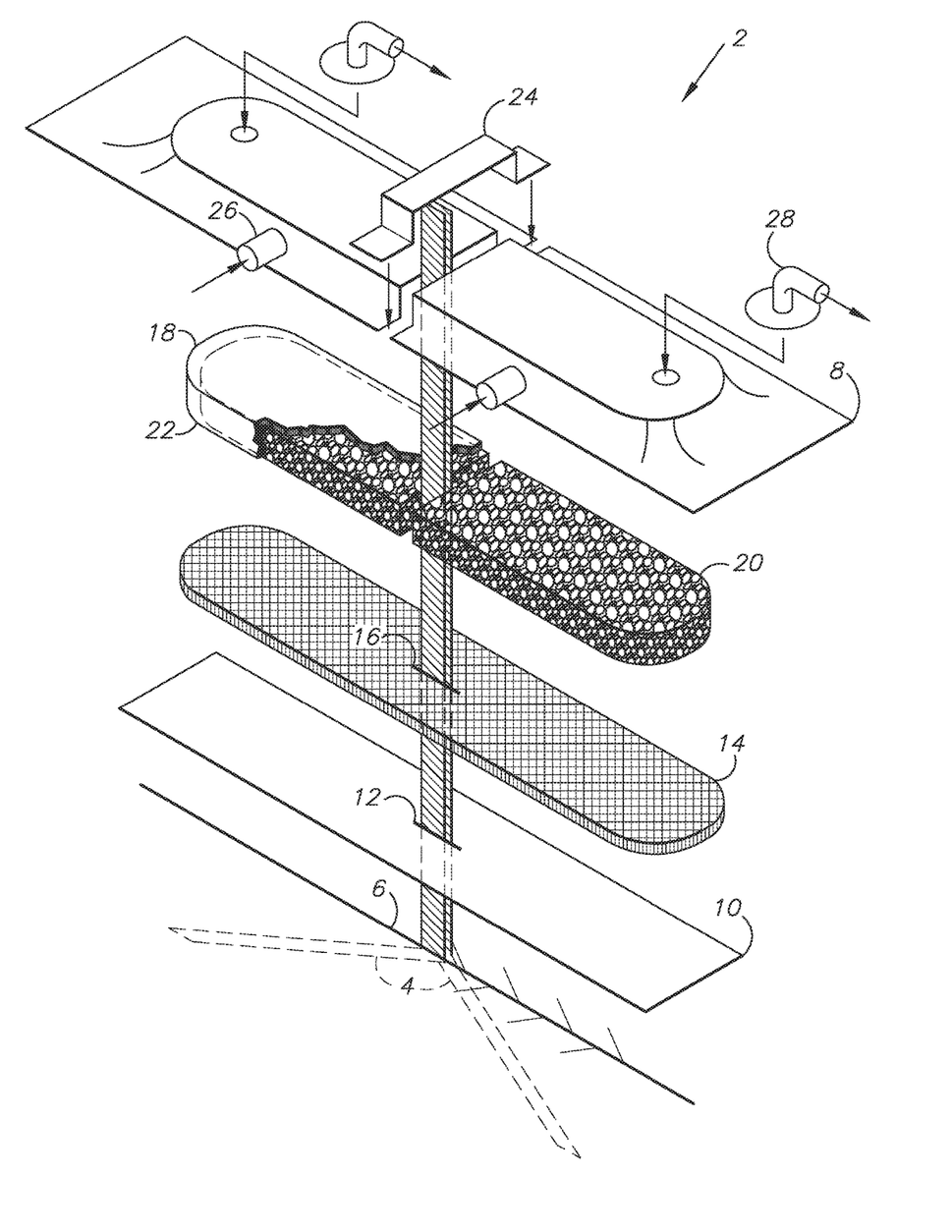
FIG. 1 is an exploded diagram of a NPWT system embodying the present invention and applied to an incision.

II. Embodiment 1—Percutaneous Drain Slip Peripheral to the Incision and to the NPWT System can be Placed "Outside" the Drape A NPWT system 2 is shown in FIG. 1 and includes percutaneous drain slips 4, which can extend into an incision 6 and terminate exteriorly at a film cover or drape 8. The slip drain 4 material can be any type of fluid impermeable thin plastic or rubber of small caliber (only a few millimeters in width) that will slide easily in the tissues and be of sufficient tensile strength that it will not tear or break as it is removed. Silicone wicks of the Swanson Drain variety are an example. They can be provided in the dressing kits or as a separate package in a roll or coil of 100 cm. This should be sufficient to run the entire length of the incision or cut into sections and run half the incision length—past either end or out the sides.

The slip drains 4 can be placed in the incision 6 and extend towards opposite ends and can exit the incision at an approximate midpoint and extend upwardly through appropriate openings or slits 12, 16 in a wick 10 and a mat 14. The slip drains 4 can extend further outwardly between the recoil transfer assembly halves 18 and terminate under the film cover or drape 8, or externally to the dressing 2. The recoil transfer assembly halves 18 can include compressible, open-cell (e.g., polyurethane) foam or sponge material cores 20 with fluid-permeable (e.g., membrane or fabric) covers 22.

An exterior connector bridge 24 is attached on the exterior of the drape 8 and can be used to cover a gap between drape sections. The dressing system 2 can thus be customized to various lengths and configurations. Fluid inlets 26 can be located in the sides of the dressing assembly 2 and fluid outlets comprising elbow-configuration fittings 28 can be placed on the top of the dressing system 2. Various fluid inlet and outlet configurations and placements can be utilized.

Alternative slip drain configurations could be utilized with different numbers of slip drains, wound interfaces and dressing exits. Moreover, various types of drain devices could be utilized and connected to external devices, including other dressings, as indicated for a particular incision or treatment procedure.

One technique embodying the present invention would be to lay a slip drain at fascial level after its closure, in the depths of the wound, or in specific planes that the surgeon feels are at risk for seroma/hematoma collection. The drain is brought from the inside to the outside through a percutaneous stab wound using a long narrow clamp from the inside and incising a tiny stab wound over the clamp tip holding it at skin level, re-grasping the drain from the outside and then pulling it through until it is flat or straight in the incision bed. Skin closure is completed and the external dressing with foam core and liner is applied and vacuum instituted. The wound is then massaged and manipulated side to side to ensure all deep layers are in good apposition. The incision, over the NPWT-incisional dressing is then rolled from the point(s) furthest away from the percutaneous drain site toward it. The egress and collection of this drainage can be enhanced by using the ubiquitously available operative suction at the percutaneous stab wound with a gauze sponge over the drain (and under it if desired). The suction picks up the drainage as it egresses and enhances its migration outward. After the rolling (or even simple manual milking), the suction is kept in place over the gauze sponge as the drain is pulled out beneath it. The skin stab wound is then sealed with a simple steri-strip or small piece of paper tape over it. The patient is then allowed to emerge from anesthesia and taken to recovery and the incisional NPWT continued as usual.

III. Embodiment 2—Drain Slip Brought Out Through the Incision or Percutaneously but still "Inside" and Under the Drape and/or the Foam and Mat of the Dressing In this embodiment, the materials provided in the "drain" kit include the above described 100 cm roll of silicone slip drain (sizes and material specifics are NOT limiting) but also a convenient size of a covering wicking fabric (e.g. 3 or 4 pieces of rayon about ½ inch wide by 4 inches in length) and sealing strips (3 or 4 pieces of hydrocolloid about 8-10 mm's wide—such as are available in the new customized Prevena NPWT kit from Kinetic Concepts, Inc. to allow edge sealing) and strips of sealing drape.

The method is similar to that described in the first embodiment except that after laying the slip drain along the fascia, it is brought up to the surface at the end or edge of the incision (can theoretically be any point judged optimal by the surgeon to evacuate potential deep space collections of drainage). Closure is completed and the drain, from the incision to a point beyond where the drape will end, is covered with the protective wicking strips (e.g. rayon). The vacuum is then applied to the external dressing, the foam core compressed and the rolling/milking and drainage evacuating procedure described above is carried out, again protecting and enhancing the evacuation point with a 4×4 gauze sponge and using the operating-room suction. The drain slip is aided in its removal under the drape by the presence of the intervening wick material which is left in place and the edge, where the drain was removed, of the wicking material beyond the drape is trimmed and the potentially open leak point of the wicking material exit site is sealed by applying a hydrocolloid strip and additional drape over this point.

An adjunctive maneuver that may aid the application of compression to the external dressing foam over the incision before the drain is extracted (as described above), now that we have, as it were, a built-in significant leak where we've run the drain slip under the drape, is to use the operative suction to draw down the foam (avoiding exhausting the battery life of the small vacuum pump), digitally pressing down on the drain-slip area to decrease the leak, and then clamping the tubing to the attachment patch on the dressing (rubber-shod clamp or similar method). The operative suction is then available to place on the drain exit point and proceed as described above. After the drain is removed and the edge sealed, the vacuum pump can be applied to the tubing and the procedure is completed. Of course, this step is not necessary if there are two suction sources in the OR or if one source is split with a Y-tube. In addition to the alternative embodiments described above, various other alternative embodiments, applications and procedures can utilize the present invention, including adaptations thereof.

It should be understood that there are many varieties and alternatives of applying these principles of draining the fluid and achieving the "set" of the operative wound—before or after the vacuum pack system is applied or compressed. The classic Swanson drain technique is to close the incision first and then use long, thin forceps to inset the drain slip between the sutures. Doing this, we can see that one option is even to just cover the drain slips with gauze pads (e.g., commonly-available 4 cm×4 cm square or other materials, sizes and configurations). Alternatively, lap tape can be applied and manually formed and molded to compress the wound to get the residual drainage out.

Embedded slip drains can be connected to an external NPWT dressing and suction (negative pressure or vacuum) can be applied. The drain slips can be brought out at any area of the incision or, as described above, percutaneously beyond the incision. These maneuvers reduce the risk of spaces where tissue is not apposed, which will subsequently become seromas and hematomas. Because of this reduced risk, the need for a Hemovac-type drain can be reduced or eliminated.

In a preferred embodiment of the present invention, one or more fluid-impermeable slip drains 4 are placed in sub-dermal planes of a wound or incision at risk for liquid-filled, space-occupying lesions. One end of each slip drain 4 is brought to the skin surface, with the excess slack pulled through the center of the incision 6 until the slip drain 4 is relatively flat and straight. The incision 6 is closed at the skin level, and an external NPWT surface dressing is applied to the skin surface surrounding the incision 6. The NPWT dressing includes a compressible core 20 and a drape 8 having adhesive configured for releasable attachment to the skin surface. The drape 8 includes output ports 28 for connection to a negative pressure source and may also include input ports 26 for supplying wound-healing factors to the wound. The dressing may also include a fluid-permeable cover 22 over the recoil core 20, a wick 10, and a mat 14. In this embodiment, the NPWT dressing includes openings or gaps 12, 16 near the midpoint of the dressing to allow the one or more slip drains 4 through the dressing. The compressible, recoil core 20 may be made up of halves 18, as shown in FIG. 1, forming such a gap.

Negative pressure, or suction, is applied to the slip drains 4 and the NPWT dressing, causing the compressible core 20 to compress. Preferably, the negative pressure source is the operating room vacuum, used immediately post-operation. Once suction is being applied, the incision 6 is massaged from side to side, putting the deep layers in a good apposition. The incision 6 is then rolled or milked from the point furthest away from the exit point of the one or more slip drains 4 towards the exit point of the slip drains 4. This allows fluid drainage to be collected from the wound 6 with the slip drains 4. Once fluid is collected from the wound 6 via the slip drains 4, the slip drains 4 are pulled out through the incision 6, maintaining suction through the NPWT dressing. After removal of the slip drains 4, a patch 24, typically made up of a small piece of drape and adhesive, is placed over the gap in the dressing to seal the dressing over the incision 6. From here, the operating room suction may be clamped and another negative pressure source connected to the NPWT dressing in preparation for or after removal of the patient from the operating room. This other negative pressure source may be a portable negative pressure pump.

Optionally, the portion of the slip drains from the skin surface to a point beyond where the drape ends may be covered with protective wicking strips. In such an embodiment, the protective wicking strips are left in place when removing the slip drains. The portion of the wicking strips beyond the drape is then trimmed, and a patch is used to seal the dressing, over the wicking strips.

IV. Additional Embodiments and Applications

A wide variety of wound dressings can be provided within the scope of the present invention. For example, variations appropriate for particular wound (including incision) conditions can be accommodated by varying the configurations, sizes, shapes and materials of the various components.

Fluid drainage characteristics along the top (i.e. distal or outer surface) of the dressing can be enhanced by placing a wicking material layer (similar to wick 10) on top of the porous transfer element 18. A slip drain, such as that shown at 4, can extend from the center of the dressing 2 or either or both ends. For example, the slip drain 4 can be split longitudinally, with each split section extending between a slip drain and an outlet port formed in the covering membrane or drape, such as that shown that 8. Moreover, the passage for the slip drain 4 can be lined with wicking material to facilitate upward or outward fluid flow. In this configuration the bottom or proximal wick layer 10 can draw fluid from the wound area for communication to the slip drain for passage upward and outward through the wicking material-lined passage to the upper (distal) wick layer. The extracted fluid is evacuated under negative pressure through fluid outlet.

The slip drain 4 can be secured to the top of the transfer element 18 for convenient extraction when the transfer element 18 is removed, e.g., in connection with a dressing change. Attaching the slip drain 4 to the transfer element 18 facilitates complete removal of the slip drain 4 and the transfer element 18, thus avoiding the necessity for the healthcare practitioner to separately extract the slip drain 4.

The slip drain 4 can extend outwardly from the upper (distal) face of the transfer element 18, forming a knuckle-like extension to facilitate externally evacuating the extracted fluid. The drape 8 can be slit or punctured to provide an outlet drain opening for coverage by a fluid outlet fitting, such as that shown at 28. A negative pressure vacuum pump, e.g., wall suction or a portable device, can be connected to the outlet fitting 28. Similar fittings can be used for introducing fluids, such as growth factors, antibiotics and pharmacologics to the wound to facilitate cell growth and wound closure.

The entire dressing assembly 2 can be prepackaged and applied in a "peel-and-place" format for convenience and efficiency. Moreover, the slip drain 4 and other elements can be trimmed to appropriate links and sizes. Various combinations and multiples of transfer elements, wicks, slip drains and inlet-outlet fittings can be used for assembling dressings for accommodating particular patient conditions, with the goal of optimizing healing outcomes. Moreover, a variety of materials can be utilized for constructing the dressing assembly elements. For example, silicone-based materials generally tend to slide easily due to their relatively low coefficients of friction, and can be formulated for relatively high tensile strength. Latex is also a suitable material choice for many applications.

Application sequences are also variable within the scope of the present invention. For example, the slip drains 4 can be tucked into the subcutaneous layers. Optionally, the slip drains 4 can be placed either before or after suturing a wound.

It is to be understood that the invention can be embodied in various forms, and is not to be limited to the examples discussed above. The range of components and configurations which can be utilized in the practice of the present invention is virtually unlimited.

The invention claimed is:

1. A negative pressure wound therapy (NWPT) dressing configured for application to a skin surface over a closed wound incision and connected to a negative pressure source, which dressing comprises:
   a fluid-permeable wick element configured for placement over the incision, said wick element configured for substantially continuously engaging skin surface around said closed wound incision;
   a fluid transfer component placed on the wick element and including an exterior surface;
   said transfer component configured for connection to the negative pressure source and transferring fluid from the incision through the wick element and to the exterior surface;
   said transfer component configured for transmitting negative pressure from the negative pressure source to the incision;
   a drape placed over the transfer component and adapted for releasable connection to a skin surface around the incision;
   an inlet fluid connection mounted on said drape and configured for introducing fluid to said transfer component;
   an outlet fluid connection mounted on said drape and configured for extracting fluid from said transfer component;
   a drain slip comprising a pair of material strips each having proximal ends placed in the incision and distal ends adapted for communicating with the negative pressure source; and said drain slip extending through the wick element and the fluid transfer component; and
   a permeable material mat placed between the wick and the transfer element and adapted for transferring fluid therebetween; and aligned slits in said wick element and said mat and slidably receiving said material strips.

2. The NPWT dressing according to claim 1, which includes:
   a component connected to the transfer component and configured for providing cell growth and wound closure fluids to said incision;
   an inflow line fluidically connecting the factor source to the transfer component; and
   an outflow line from the transfer component.

3. The NPWT dressing according to claim 1, which includes:
   said drain slip comprising a fluid-impermeable material and having a proximal end adapted for placement in the incision and a distal end communicating with the negative pressure source.

4. The NPWT dressing according to 1, which includes:
   said material strip proximal ends being configured for placement in spaced relation within the incision; and
   said material strips generally being respectively adjacent to each other distally from said proximal ends.

5. The NPWT dressing according to claim 1, which includes:
   said transfer component comprising first and second sections positioned adjacent to each other; and
   said drain slip extending between said transfer component sections.

6. The NPWT dressing according to claim 5, which includes:
   each said transfer component section having an elongated configuration with a first end and a second end;

said transfer component section first ends being positioned in abutting relation to each other with said transfer component sections being configured for fluidic transfer therebetween; and
said drain slip extending between said transfer component section first ends.

7. The NPWT dressing according to claim 6, which includes:
said drape comprising first and second sections positioned over said first and second transfer component sections respectively.

8. The NPWT dressing according to claim 7, which includes:
a drape bridging strip placed over said transfer component section first ends and said drape sections for closing said drape and covering relation over said transfer component, an outlet fluid connection mounted on said drape and configured for extracting fluid from said transfer component.

9. The NPWT dressing according to claim 8, which includes:
an inlet fluid connection mounted on said drape and configured for introducing fluid to said transfer component; and
an outlet fluid connection mounted on said drape and configured for extracting fluid from said transfer component.

10. A negative pressure wound therapy (NPWT) dressing configured for application to a skin surface over a closed wound incision and configured for connection to a negative pressure source, which dressing comprises:
a fluid-permeable wick element configured for placement over the incision, said wick element configured for substantially continuously engaging skin surface around said closed wound incision;
a fluid-permeable wick element adapted for placement over the incision;
a fluid transfer component placed on the wick element and including an exterior surface;
said transfer component configured for connection to the negative pressure source and transferring fluid from the incision through the wick element and to the exterior surface;
said transfer component configured for transmitting negative pressure from the negative pressure source to the incision;
a drape placed over the transfer component and adapted for releasable connection to a skin surface around the incision;
an inlet fluid connection mounted on said drape and configured for introducing fluid to said transfer component;
an outlet fluid connection mounted on said drape and configured for extracting fluid from said transfer component;
a component connected to the transfer component and configured for providing a cell manipulating factor source;
an inflow line fluidically connecting the factor source to the transfer component;
an outflow line from the transfer component;
a drain slip comprising a pair of material strips each having proximal ends placed in the incision and distal ends adapted for communicating with the negative pressure source; and said drain slip extending through the wick element and the fluid transfer component; and a permeable material mat placed between the wick and the transfer element and adapted for transferring fluid therebetween; and aligned slits in said wick element and said mat and slidably receiving said material strips.

11. The NPWT dressing according to claim 10, which includes:
said material strip proximal ends being configured for placement in spaced relation within the incision; and
said material strips generally being respectively adjacent to each other distally from said proximal ends.

12. The NPWT dressing according to claim 10, which includes:
said transfer component comprising first and second sections positioned adjacent to each other;
said drain slip extending between said transfer component sections;
each said transfer component section having an elongated configuration with a first end and a second end;
said transfer component section first ends being positioned in abutting relation to each other with said transfer component sections being configured for fluidic transfer therebetween; and
said drain slip extending between said transfer component section first ends.

13. The NPWT dressing according to claim 12, which includes:
said drape comprising first and second sections positioned over said first and second transfer component sections respectively; and
a drape bridging strip placed over said transfer component section first ends and said drape sections for closing said drape and covering relation over said transfer component.

14. The NPWT dressing according to claim 13, which includes:
an inlet fluid connection mounted on said drape and configured for introducing fluid to said transfer component; and
an outlet fluid connection mounted on said drape and configured for extracting fluid from said transfer component.

15. A negative pressure wound therapy (NPWT) method, which comprises the steps of:
placing a fluid-permeable wick element over a closed wound incision with said wick element configured for substantially continuously engaging skin surface around said closed wound incision;
placing a transfer component over the wick;
draping said transfer component with a membrane;
attaching said membrane to a patient's skin surface around said transfer component;
extending a drain slip proximal end into the wound;
extending the drain slip through the wick and the transfer component;
applying a negative pressure to said transfer component;
extracting fluid from said wound via said wick, transfer component and drain slip,
said drain slip comprising a pair of material strips each having proximal ends placed in the incision and distal ends adapted for communicating with the negative pressure source; and said drain slip extending through the wick element and the fluid transfer component; and
placing a permeable material mat between the wick and the transfer element and adapted for transferring fluid therebetween; and aligned slits in said wick element and said mat and slidably receiving said material strips.

16. The NPWT method according to claim 15, which includes additional steps of:
- placing a fluid-permeable mat between the wick and the transfer component;
- transferring fluid under negative pressure from the mat to the transfer component; and
- forming said transfer component with a compressible, open-cell foam core.

17. The NPWT method according to claim 16, which includes the additional step of:
- enclosing said transfer component core with a permeable membrane flexible cover;
- placing drain tubing within said incision;
- extracting fluid from said incision with said drain tubing;
- setting edges of said wound in apposition to each other; and
- drawing said wound edges together in abutting relation using NPWT applied via said transfer component.

\* \* \* \* \*